United States Patent [19]

Kirino et al.

[11] 4,274,862
[45] Jun. 23, 1981

[54] N-DIMETHYLBENZYLACETAMIDE DERIVATIVES, AND THEIR PRODUCTION AND USE

[75] Inventors: Osamu Kirino, Ashiya; Shunichi Hashimoto, Toyonaka; Hiroshi Matsumoto, Takarazuka; Hiromichi Oshio, Osaka, all of Japan

[73] Assignee: Sumitomo Chemical Company, Limited, Osaka, Japan

[21] Appl. No.: 91,871

[22] Filed: Nov. 7, 1979

[30] Foreign Application Priority Data

Nov. 13, 1978 [JP] Japan ................................. 53-140071
Nov. 15, 1978 [JP] Japan ................................. 53-141412

[51] Int. Cl.³ ............... C07C 103/737; C07C 103/375; C07C 103/38; A01N 9/20
[52] U.S. Cl. ..................................... 71/118; 564/123; 564/189; 564/191; 564/202; 564/212; 564/219; 71/3; 71/65; 71/79
[58] Field of Search .......... 260/557 R, 562 B, 562 A, 260/562 R; 71/118; 564/189, 191, 123, 202, 212, 219

[56] References Cited

U.S. PATENT DOCUMENTS

| | | | |
|---|---|---|---|
| 3,045,043 | 7/1962 | Schmitt et al. | 260/562 A X |
| 3,346,362 | 10/1967 | Diveley | 71/118 |
| 3,498,781 | 3/1970 | Buntin | 71/118 |
| 3,644,521 | 2/1972 | Buntin | 71/118 X |
| 3,689,557 | 9/1972 | McCaully et al. | 260/562 A X |

FOREIGN PATENT DOCUMENTS 48-88228 11/1973 Japan.
54-5005 1/1979 Japan.

OTHER PUBLICATIONS

CA 68:48 859t (1968).
Angew. Chem., 78, 932 (1966).
J. Chem. Soc., 1977, 694.
J. Amer. Chem. Soc., 71, 3929 (1949) and 55, 4209 (1933).

Primary Examiner—Thomas A. Waltz
Attorney, Agent, or Firm—Birch, Stewart, Kolasch & Birch

[57] ABSTRACT

A compound of the formula:

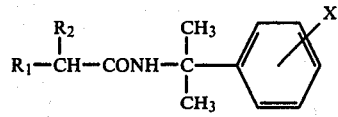

wherein X is a hydrogen atom, a methyl group, a methoxy group or a chlorine atom, $R_1$ is a $C_2$-$C_7$ alkyl group or a $C_5$-$C_7$ cycloalkyl group and $R_2$ is a hydrogen atom, a halogen atom, a $C_1$-$C_4$ alkyl group or a methoxy group, or when $R_1$ and $R_2$ are taken together, they represent a $C_4$-$C_6$ alkylene group, provided that when $R_1$ is a tertiary alkyl group, $R_2$ does not represent a halogen atom, herbicidal compositions containing the above-mentioned compounds and methods for controlling weeds utilizing the same.

14 Claims, No Drawings

N-DIMETHYLBENZYLACETAMIDE DERIVATIVES, AND THEIR PRODUCTION AND USE

The present invention relates to N-dimethylbenzylacetamide derivatives, and their production and use. More particularly, it relates to N-dimethylbenzylacetamide derivatives and herbicidal compositions containing the same, and their preparation processes.

The said N-dimethylbenzylacetamide derivatives are representable by the formula (I):

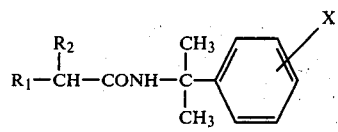

wherein X is a hydrogen atom, a methyl group, a methoxy group or a chlorine atom, $R_1$ is a $C_2$–$C_7$ alkyl group or a $C_5$–$C_7$ cycloalkyl group and $R_2$ is a hydrogen atom, a halogen atom, a $C_1$–$C_4$ alkyl group or a methoxy group, or when $R_1$ and $R_2$ are taken together, they represent a $C_4$–$C_6$ alkylene group, provided that when $R_1$ is a tertiary alkyl group, $R_2$ does not represent a halogen atom.

The term "halogen atom" as hereinabove used is intended to mean chlorine, bromine, fluorine and iodine, inclusively.

As the result of an extensive study, it has been found that the N-dimethylbenzylacetamide derivatives (I) have a strong herbicidal activity against a wide variety of weeds. For instance, they can exert a notable controlling or eradicating activity on the following annual and perennial weeds by pre-emergence soil treatment or post-emergence foliar or soil treatments: Gramineae weeds such as barnyard-grass (*Echinochloa crus-galli*), large crabgrass (*Digitaria sanguinalis*), green foxtail (*Setaria viridis*), Cyperaceae weeds such as yellow nutsedge (*Cyperus esculentus*), nutsedge sp. (*Cyperus difformis*), purple nutsedge (*Cyperus rotundus*), Scirpus Hotarui, slender spikerush (*Eleocharis acicularis*), *Cyperus serotinus* and *Eleocharis kuroguwai*, Amaranthaceae weeds such as redroot pigweed (*Amaranthus retroflexus*), Chenopodiaceae weeds such as common lambsquarters (*Chenopodium album*), Polygonaceae such as ladysthumb (*Polygonum persicaria*) and curlydock (*Rumex japonicus*), Pontederiaceae such as *Monochoria vaginalis*, Scrophulariaceae such as false pimpernel (*Lindernia pyxidaria*), Alismataceae such as arrowhead (*Sagittaria pygmaea*), Compositae such as dandelion (*Taraxacum officinale*), Oxalidaceae such as Woodsorrel (*Oxalis corniculata*), etc. Thus, their herbicidal activity is effective in controlling and eradicating not only field weeds but also paddy field weeds.

Advantageously, the N-dimethylbenzylacetamide derivatives (I) do not produce any injury on various crop plants such as rice, soybean, cotton, corn, peanut, sunflower, rape and potato and numerous vegetables such as lettuce, cabbage, tomato, cucumber and carrot.

Accordingly, the N-dimethylbenzylacetamide derivatives (I) are useful as herbicides applicable for field crops and vegetables as well as paddy rice. They are also useful as herbicides to be employed for orchard, lawn, pasture, tea garden, mulberry field, rubber plantation, forest, etc.

Japanese Patent Publication (unexamined) No. 88228/1973 and U.S. Pat. No. 3,498,781 disclose some pivalic acid amide derivatives, which are somewhat similar to the N-dimethylbenzylacetamide derivatives (I) in chemical structure and which have a herbicidal activity. However, the herbicidal activity of the N-dimethylbenzylacetamide derivatives (I) is generally more excellent than that of the pivalic acid amide derivatives. It is particularly notable that, in comparison with the pivalic acid amide derivatives, the N-dimethylbenzylacetamide derivatives (I) exert an extremely high herbicidal effect on annual and perennial weeds in paddy fields without any phytotoxicity on rice plants. Further, the N-dimethylbenzylacetamide derivatives (I) are quite characteristic in being highly effective for controlling or eradicating perennial Cyperaceae weeds.

The N-dimethylbenzylacetamide derivatives (I) can be produced by reacting an acetic acid derivative of the formula (II):

wherein $R_1$ and $R_2$ are each as defined above, or its reactive derivative with a dimethylbenzylamine derivative of the formula (III):

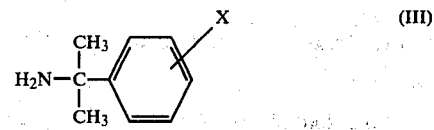

wherein X is as defined above.

The acetic acid derivative (II) may be synthesized, for instance, by the method as disclosed in Angew. Chem., 78, 932 (1966) and J.Chem.Soc., 1977, 694. The dimethylbenzylamine derivative (III) is obtainable, for instance, by the method as disclosed in J.Am.Chem. Soc., 71, 3929 (1949).

For the reaction, the acetic acid derivative (II) or its reactive derivative and the dimethylbenzylamine derivatives (III) may be used in an equivalent ratio of 0.4 to 1.5:1, preferably 0.5 to 1.1:1. The reaction may be carried out in the presence or absence of an inert solvent. Examples of the inert solvent are hydrocarbons (e.g. benzene, toluene, xylene), halogenated hydrocarbons (e.g. chlorobenzene, methylene chloride, chloroform, carbon tetrachloride), ethers (e.g. diisopropyl ether, tetrahydrofuran, dioxane), alcohols (e.g. methanol, ethanol, isopropanol), ketones (e.g. acetone, methylethylketone, methylisobutylketone), esters (e.g. ethyl acetate), nitriles (e.g. acetonitrile), dimethylsulfoxide, dimethylformamide, water, etc. Among them, particularly preferred is benzene. The reaction may be carried out within a wide range of temperature from the freezing point to the boiling point of the solvent, preferably from 0° C. to the boiling temperature of the solvent. If necessary, cooling or heating may be adopted.

As the acetic acid derivative (II) or its reactive derivative, there may be used free acid, acid anhydride, acid chloride, acid bromide, acid ester, etc. Depending upon the kind of the reactive derivative, an appropriate reaction aid such as a condensing agent, a dehydrating agent, an acid-eliminating agent or a catalyst may be employed in the reaction. In case of the free acid, dicyclohexylcarbodiimide, phosphorus pentachloride, phosphorus trichloride, phosphorus tribromide, thionyl chloride, sodium hydroxide, potassium hydroxide, sodium methoxide, sodium ethoxide, triethylamine, pyridine, quinoline, isoquinoline, N,N-dimethylaniline, N,N-diethylaniline, N-methylmorpholine, etc. are examples of the reaction aid. In case of the acid chloride or acid bromide, sodium hydroxide, potassium hydroxide, sodium methoxide, sodium ethoxide, triethylamine, pyridine, quinoline, isoquinoline, N,N-dimethylaniline, N,N-diethylaniline, N-methylmorpholine, sodium acetate, etc., preferably triethylamine, may be used as the reaction aid. When the reaction aid is employed, its amount may be from a catalytic amount to 1.5 equivalent, preferably from 0.95 to 1.1 equivalent to the material to be eliminated from the starting compounds as the result of the reaction.

The recovery of the reaction product from the reaction mixture may be carried out in a per se conventional manner. For instance, the reaction mixture is filtered and/or washed with water, followed by distillation for removal of the solvent to give the reaction product, i.e. the N-dimethylbenzylacetamide derivative (I). When desired, this reaction product may be purified by a per se conventional procedure such as recrystallization from an appropriate solvent such as benzene, toluene, n-hexane, methanol, ethanol, chloroform or methylisobutylketone.

Practical embodiments of the preparation of the N-dimethylbenzylacetamide derivatives (I) are illustratively shown in the following examples.

EXAMPLE 1

Into a 200 ml four-necked flask, there were charged toluene (100 ml), α,α-dimethylbenzylamine (9 g) and pyridine (5.8 g), and α-methyl-tert-butylacetyl chloride (9.9 g) was dropwise added thereto while stirring at room temperature. Stirring was continued for 3 hours. The reaction mixture was washed with water to remove pyridine hydrochloride. After the toluene layer was dried over anhydrous sodium sulfate, the solvent was distilled off under reduced pressure. The obtained residue was recrystallized from ethanol to give 13.8 g of N-(α,α-dimethylbenzyl)-α-methyl-tert-butylacetamide. M.P., 162.5°–163.5° C.

Elementary analysis:
Calcd.: C, 77.68%; H, 10.19%; N, 5.66%. Found: C, 77.82%; H, 10.36%; N, 5.83%.

EXAMPLE 2

Into a 200 ml four necked flask, there were charged benzene (100 ml), α,α-dimethylbenzylamine (9 g) and triethylamine (7.4 g), tert-butylacethyl chloride (9.5 g) was dropwise added thereto while stirring at room temperature. Stirring was continued for 3 hours. The reaction mixture was washed with water to remove triethylamine hydrochloride. After the benzene layer was dried over anhydrous sodium sulfate, the solvent was distilled off under reduced pressure. The obtained residue was recrystallized from ethanol to give 13.5 g of N-(α,α-dimethylbenzyl)-tert-butylacetamide. M.P., 159°–160.5° C.

Elementary analysis:
Calcd.: C, 77.21%; H, 9.93%; N, 6.00%. Found: C, 77.25%; H, 10.03%; N, 6.01%.

EXAMPLE 3

(1) Into a 200 ml four necked flask, there were charged benzene (100 ml), α,α-dimethylbenzylamine (9 g) and triethylamine (7.4 g), and α-bromo-isovaleryl chloride (13.3 g) was dropwise added thereto while stirring at room temperature. Stirring was continued for 3 hours. The reaction mixture was washed with water to remove triethylamine hydrochloride. After the benzene layer was dried over anhydrous sodium sulfate, the solvent was distilled off under reduced pressure. The obtained residue was recrystallized from ethanol to give 16.9 g of N-(α,α-dimethylbenzyl)-α-bromo-isovaleramide. M.P., 128°–129.5° C.

Elementary analysis:
Calcd.: C, 56.39%; H, 6.76%; N, 4.70%; Br, 26.79%. Found: C, 56.21%; H, 6.47%; N. 4.78%; Br, 26.82%.

(2) Into a 500 ml four-necked flask, there were charged methylisobutylketone (150 ml), α,α-dimethylbenzylamine (27.0 g) and triethylamine (21.2 g), and α-bromo-isovaleryl chloride (40.0 g) was dropwise added thereto while stirring at room temperature. Stirring was continued for 3 hours. After completion of the reaction, water (200 ml) was added thereto and the reaction mixture was gradually heated to remove methylisobutylketone, followed by cooling at room temperature. The precipitated crystals were filtered, washed with water, dried and recrystallized from ethanol to give N-(α,α-dimethylbenzyl)-α-bromo-isovaleramide (51.9 g).

In the same manner as above, there can be produced other N-dimethylbenzylacetamide derivatives (I), of which some specific examples will be shown in Table 1 but without any intention to limit the scope of the invention thereto:

TABLE 1

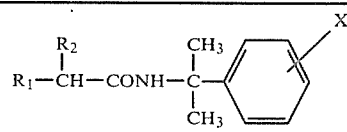

| Compound No. | R₁ | R₂ | X | Melting point (°C.) | Elementary analysis (%) | | | |
|---|---|---|---|---|---|---|---|---|
| | | | | | | C | H | N | Halogen |
| 1 | i-C₃H₇ | H | H | 97–99 | Calcd. | 76.67 | 9.65 | 6.39 | |
| | | | | | Found | 76.58 | 9.82 | 6.45 | |
| 2 | i-C₄H₉ | H | H | 80–81 | Calcd. | 77.21 | 9.93 | 6.00 | |
| | | | | | Found | 77.20 | 10.09 | 5.97 | |
| 3 | s-C₄H₉ | H | H | 78–79 | Calcd. | 77.21 | 9.93 | 6.00 | |
| | | | | | Found | 77.27 | 10.07 | 5.99 | |
| 4 | t-C₄H₉ | H | H | 159–160.5 | Calcd. | 77.21 | 9.93 | 6.00 | |
| | | | | | Found | 77.25 | 10.03 | 6.01 | |

TABLE 1-continued $$R_1-CH(R_2)-CONH-C(CH_3)_2-C_6H_4-X$$

| Compound No. | R₁ | R₂ | X | Melting point (°C.) | | C | H | N | Halogen |
|---|---|---|---|---|---|---|---|---|---|
| 5 | t-C₄H₉ | H | 4-CH₃ | 170–172 | Calcd. | 77.68 | 10.19 | 5.66 | |
| | | | | | Found | 77.77 | 10.20 | 5.39 | |
| 6 | n-C₃H₇-C(CH₃)₂- | H | H | 91–92.5 | Calcd. | 78.11 | 10.41 | 5.36 | |
| | | | | | Found | 77.99 | 10.52 | 5.39 | |
| 7 | i-C₃H₇-C(CH₃)₂- | H | H | 113.5–115 | Calcd. | 78.11 | 10.41 | 5.36 | |
| | | | | | Found | 78.32 | 10.51 | 5.19 | |
| 8 | C₂H₅-C(CH₃)(C₂H₅)- | H | H | 95–96 | Calcd. | 78.11 | 10.41 | 5.36 | |
| | | | | | Found | 78.12 | 10.68 | 5.24 | |
| 9 | n-C₄H₉-C(CH₃)₂- | H | H | 72–73 | Calcd. | 78.49 | 10.61 | 5.09 | |
| | | | | | Found | 78.38 | 10.83 | 5.27 | |
| 10 | cyclopentyl | H | H | 121–122 | Calcd. | 78.32 | 9.45 | 5.71 | |
| | | | | | Found | 78.44 | 9.51 | 5.63 | |
| 11 | cyclohexyl | H | H | 124–126 | Calcd. | 78.72 | 9.71 | 5.40 | |
| | | | | | Found | 78.88 | 9.70 | 5.29 | |
| 12 | 1-methylcyclopentyl | H | H | 126–127 | Calcd. | 78.72 | 9.71 | 5.40 | |
| | | | | | Found | 78.94 | 9.92 | 5.54 | |
| 13 | 1-methylcyclohexyl | H | H | 138–139 | Calcd. | 79.07 | 9.95 | 5.12 | |
| | | | | | Found | 79.19 | 9.82 | 5.03 | |
| 14 | n-C₃H₇ | CH₃ | H | 93–95 | Calcd. | 77.21 | 9.93 | 6.00 | |
| | | | | | Found | 77.28 | 10.15 | 5.99 | |
| 15 | i-C₃H₇ | CH₃ | H | 89–91 | Calcd. | 77.21 | 9.93 | 6.00 | |
| | | | | | Found | 77.33 | 9.87 | 6.12 | |
| 16 | i-C₃H₇ | i-C₃H₇ | H | 106–109 | Calcd. | 78.11 | 10.41 | 5.36 | |
| | | | | | Found | 78.22 | 10.53 | 5.10 | |
| 17 | n-C₄H₉ | C₂H₅ | H | 117.5–119 | Calcd. | 78.11 | 10.41 | 5.36 | |
| | | | | | Found | 78.03 | 10.29 | 5.42 | |
| 18 | t-C₄H₉ | CH₃ | H | 162.5–163.5 | Calcd. | 77.68 | 10.19 | 5.66 | |
| | | | | | Found | 77.82 | 10.36 | 5.83 | |
| 19 | t-C₄H₉ | CH₃ | 2-CH₃ | 145–147 | Calcd. | 78.11 | 10.41 | 5.36 | |
| | | | | | Found | 78.03 | 10.61 | 5.43 | |
| 20 | t-C₄H₉ | CH₃ | 3-CH₃ | 134–135.5 | Calcd. | 78.11 | 10.41 | 5.36 | |
| | | | | | Found | 78.15 | 10.65 | 5.40 | |
| 21 | t-C₄H₉ | CH₃ | 4-CH₃ | 177–179 | Calcd. | 78.11 | 10.41 | 5.36 | |
| | | | | | Found | 78.23 | 10.49 | 5.20 | |
| 22 | t-C₄H₉ | CH₃ | 4-Cl | 175–177.5 | Calcd. | 68.19 | 8.58 | 4.97 | 12.58 (Cl) |
| | | | | | Found | 68.30 | 8.42 | 4.75 | 12.61 (Cl) |
| 23 | t-C₄H₉ | C₂H₅ | H | 169.5–170.5 | Calcd. | 78.11 | 10.41 | 5.36 | |
| | | | | | Found | 78.32 | 10.45 | 5.36 | |
| 24 | t-C₄H₉ | C₂H₅ | 4-CH₃ | 160–161 | Calcd. | 78.49 | 10.61 | 5.09 | |
| | | | | | Found | 78.61 | 10.77 | 5.01 | |
| 25 | t-C₄H₉ | n-C₃H₇ | H | 131–132.5 | Calcd. | 78.49 | 10.61 | 5.09 | |
| | | | | | Found | 78.56 | 10.54 | 5.23 | |
| 26 | t-C₄H₉ | i-C₄H₉ | H | 132–133.5 | Calcd. | 78.84 | 10.79 | 4.84 | |
| | | | | | Found | 78.96 | 10.87 | 4.65 | |
| 27 | t-C₄H₉ | OCH₃ | H | 95–97 | Calcd. | 72.97 | 9.57 | 5.32 | |
| | | | | | Found | 72.71 | 9.64 | 5.06 | |
| 28 | C₂H₅ | Cl | H | 109–110 | Calcd. | 65.13 | 7.57 | 5.84 | 14.79 (Cl) |

TABLE 1-continued $$R_1-\underset{\underset{H}{|}}{C}H-CONH-\underset{\underset{CH_3}{|}}{\overset{\overset{CH_3}{|}}{C}}-\underset{}{\text{(phenyl)}}-X$$
(with $R_2$ on the CH)

| Compound No. | $R_1$ | $R_2$ | X | Melting point (°C.) | | C | H | N | Halogen |
|---|---|---|---|---|---|---|---|---|---|
| | | | | | Found | 65.32 | 7.75 | 5.90 | 14.97 (Cl) |
| 29 | n-$C_3H_7$ | Br | H | 111.5–113.5 | Calcd. | 56.39 | 6.76 | 4.70 | 26.79 (Br) |
| | | | | | Found | 56.42 | 6.91 | 4.77 | 26.84 (Br) |
| 30 | i-$C_3H_7$ | Br | H | 128–129.5 | Calcd. | 56.39 | 6.76 | 4.70 | 26.79 (Br) |
| | | | | | Found | 56.21 | 6.47 | 4.78 | 26.82 (Br) |
| 31 | i-$C_3H_7$ | Br | 2-$OCH_3$ | 89–91 | Calcd. | 54.89 | 6.76 | 4.27 | 24.34 (Br) |
| | | | | | Found | 54.75 | 6.80 | 4.33 | 24.49 (Br) |
| 32 | i-$C_3H_7$ | Br | 3-$CH_3$ | 105–107 | Calcd. | 57.70 | 7.10 | 4.49 | 25.59 (Br) |
| | | | | | Found | 57.59 | 7.21 | 4.38 | 25.63 (Br) |
| 33 | i-$C_3H_7$ | I | H | 147–149 | Calcd. | 48.71 | 5.84 | 4.06 | 36.76 (I) |
| | | | | | Found | 48.79 | 5.93 | 3.84 | 36.92 (I) |
| 34 | n-$C_4H_9$ | Br | H | 90–91.5 | Calcd. | 57.70 | 7.10 | 4.49 | 25.59 (Br) |
| | | | | | Found | 57.86 | 7.28 | 4.64 | 25.46 (Br) |
| 35 | s-$C_4H_9$ | Br | H | 99.5–101 | Calcd. | 57.70 | 7.10 | 4.49 | 25.59 (Br) |
| | | | | | Found | 57.90 | 7.24 | 4.58 | 25.55 (Br) |
| 36 | s-$C_4H_9$ | Br | 4-$CH_3$ | 108–109.5 | Calcd. | 58.90 | 7.41 | 4.29 | 24.49 (Br) |
| | | | | | Found | 59.11 | 7.63 | 4.14 | 24.37 (Br) |
| 37 | cyclopentyl | Br | H | 146.5–148 | Calcd. | 59.27 | 6.84 | 4.32 | 24.64 (Br) |
| | | | | | Found | 59.38 | 6.65 | 4.19 | 24.61 (Br) |
| 38 | cyclohexyl | Br | H | 146–147.5 | Calcd. | 60.36 | 7.15 | 4.14 | 23.62 (Br) |
| | | | | | Found | 60.18 | 7.09 | 4.30 | 23.58 (Br) |
| 39 | —$(CH_2)_4$— | | H | 134–135 | Calcd. | 77.88 | 9.15 | 6.05 | |
| | | | | | Found | 77.81 | 9.34 | 5.93 | |
| 40 | —$(CH_2)_5$— | | H | 158–159 | Calcd. | 78.32 | 9.45 | 5.71 | |
| | | | | | Found | 78.53 | 9.57 | 5.52 | |
| 41 | —$(CH_2)_6$— | | H | 176–177.5 | Calcd. | 78.72 | 9.91 | 5.40 | |
| | | | | | Found | 78.94 | 9.82 | 5.34 | |

In the practical usage of the N-dimethylbenzylacetamide derivatives (I), they may be applied as such or in any preparation form such as granules, fine granules, dusts, coarse dusts, wettable powders, emulsifiable concentrates, flowable formulations, aqueous concentrates or oily suspensions.

In producing such preparation form, solid or liquid carriers may be used. As for the solid carrier, there may be given mineral powders (e.g. kaolin, bentonite, clay, montmorillonite, talc, diatomaceous earth, mica, vermiculite, gypsum, calcium carbonate, apatite), vegetable powders (e.g. soybean powder, flour, wooden powder, tobacco powder, starch, crystalline cellulose), high molecular weight compounds (e.g. petroleum resin, polyvinyl chloride, dammar gum, ketone resin), alumina, wax and the like.

As for the liquid carrier, there may be given kerosene, alcohols (e.g. methanol, ethanol, ethylene glycol, benzyl alcohol), aromatic hydrocarbons (e.g. toluene, benzene, xylene, methylnaphthalene), halogenated hydrocarbons (e.g. chloroform, carbon tetrachloride, monochlorobenzene), ethers (e.g. dioxane, tetrahydrofuran), ketones (e.g. acetone, methylethylketone, cyclohexanone, isophorone), esters (e.g. ethyl acetate, butyl acetate, ethylene glycol acetate), acid amides (e.g. dimethylformamide), nitriles (e.g. acetonitrile), ether alcohols (e.g. ethylene glycol ethyl ether), water and the like.

A surface active agent used for emulsification, dispersion or spreading may be any of the non-ionic, anionic, cationic and amphoteric type of agents. Examples of the surface active agent include polyoxyethylene alkyl ethers, polyoxyethylene alkylaryl ethers, polyoxyethylene fatty acid esters, sorbitan fatty acid esters, polyoxyethylene sorbitan fatty acid esters, oxyethylene-oxypropylene polymers, polyoxyethylene alkyl phosphates, fatty acid salts, alkyl sulfates, alkyl sulfonates, alkylaryl sulfonates, alkyl phosphates, polyoxyethylene alkyl sulfates, quaternary ammonium salts and the like. But, the surface active agent is not of course limited to these compounds. And, if necessary, gelatin, casein, sodium alginate, starch, agar, polyvinyl alcohol or the like may be used as an auxiliary agent.

In the preparation of a herbicidal composition, the content of the N-dimethylbenzylacetamide derivative (I) may be usually from 0.05 to 95% by weight, preferably from 3 to 50% by weight.

Practical embodiments of the herbicidal composition according to the invention are illustratively shown in the following examples wherein parts and % are by weight.

PREPARATION EXAMPLE 1

Fifty parts of Compound No. 4, 2.5 parts of a dodecylbenzenesulfonate, 2.5 parts of a ligninsulfonate and 45 parts of diatomaceous earth are well mixed while being powdered to obtain a wettable powder.

PREPARATION EXAMPLE 2

Thirty parts of Compound No. 16, 10 parts of emulsifier ("Sorpol SM-100" manufactured by Toho Chemical Co., Ltd.) and 60 parts of xylene are well mixed to obtain an emulsifiable concentrate.

PREPARATION EXAMPLE 3

Five parts of Compound No. 23, 1 part of white carbon, 5 parts of a ligninsulfonate and 89 parts of clay are well mixed while being powdered. The mixture is then well kneaded with water, granulated and dried to obtain a granule.

PREPARATION EXAMPLE 4

Thirty parts of Compound No. 30, 1 part of isopropyl phosphate, 66 parts of clay and 30 parts of talc are well mixed while being powdered. The mixture is then kneaded with water, granulated and dried to obtain a granule.

PREPARATION EXAMPLE 5

Fourty parts of bentonite, 5 parts of a ligninsulfonate and 55 parts of clay are well mixed while being powdered. The mixture is then well kneaded with water, granulated and dried to obtain a granule containing no active ingredient. The granule is then impregnated with 5 parts of Compound No. 35 dissolved in acetone. Subsequent removal of acetone gives a granule.

PREPARATION EXAMPLE 6

Ninety-five parts of bentonite of 16–48 mesh is impregnated with 5 parts of Compound No. 38 dissolved in acetone. Subsequent removal of acetone gives a granule.

The N-dimethylbenzylacetamide derivative (I) may be used together with other herbicides to improve their activity as herbicides, and in some cases, a synergistic effect may be expected. As the herbicides to be mixed with, there may be given phenoxy series herbicides such as 2,4-dichlorophenoxyacetic acid, 2-methyl-4-chlorophenoxyacetic acid and 2-methyl-4-chlorophenoxybutyric acid (including esters and salts thereof); benzoic acid series herbicides such as 3,6-dichloro-2-methoxybenzoic acid and 2,5-dichloro-3-aminobenzoic acid; diphenyl ether series herbicides such as 2,4-dichlorophenyl-4'-nitrophenyl ether, 2,4,6-trichlorophenyl-4'-nitrophenyl ether, 2-chloro-4-trifluoromethylphenyl-3'-ethoxy-4'-nitrophenyl ether, 2,4-dichlorophenyl-4'-nitro-3'-methoxyphenyl ether, 2,4-dichlorophenyl-3'-methoxycarbonyl-4'-nitrophenyl ether and sodium 5-(2'-chloro-4'-trifluoromethylphenoxy)-2-nitrobenzoate; triazine series herbicides such as 2-chloro-4,6-bisethylamino-1,3,5-triazine, 2-chloro-4-ethylamino-6-isopropylamino-1,3,5-triazine, 2-methylthio-4,6-bisethylamino-1,3,5-triazine, 2-methylthio-4,6-bisisopropylamino-1,3,5-triazone and 4-amino-6-tert-butyl-3-methylthio-1,2,4-triazine-5-one; urea series herbicides such as 3-(3,4-dichlorophenyl)-1,1-dimethylurea, 3-(3,4-dichlorophenyl)-1-methoxy-1-methylurea, 1-(2,2-dimethylbenzyl)-3-p-tolylurea and 1-(2,2-dimethylbenzyl)-3-methyl-3-phenylurea; carbamate series herbicides such as isopropyl-N-(3-chlorophenyl)carbamate and methyl-N-(3,4-dichlorophenyl)carbamate; thiolcarbamate series herbicides such as S-ethyl-N,N-dipropylthiolcarbamate, S-(4-chlorobenzyl)-N,N-diethylthiolcarbamate, S-ethyl-N,N-hexamethylenethiolcarbamate, S-2,3-dichloroallyl-N,N-diisopropylthiolcarbamate and S-ethyl-N,N-dibutylthiolcarbamate; acid anilide series herbicides such as 3,4-dichloropropionanilide, N-methoxymethyl-2,6-diethyl-α-chloroacetanilide, 2-chloro-2',6'-diethyl-N-butoxymethylacetanilide, 2-chloro-2',6'-diethyl-N-(n-propoxyethyl)acetanilide and N-chloroacetyl-N-(2,6-diethylphenyl)glycineethyl ester; uracil series herbicides such as 5-bromo-3-sec-butyl-6-methyluracil and 3-cyclohexyl-5,6-trimethyleneuracil; pyridinium chloride series herbicides such as 1,1'-dimethyl-4,4'-bispyridinium chloride; phosphorus series herbicides such as N-(phosphonomethyl)glycine, O-ethyl-O-(2-nitro-5-methylphenyl)-N-sec-butylphosphoroamidothioate, S-(2-methyl-1-piperidylcarbonylmethyl) O,O-di-n-propyldithiophosphate and S-(2-methyl-1-piperidylcarbonylmethyl), O,O-diphenyldithiophosphate; toluidine series herbicides such as α,α,α-trifluoro-2,6-dinitro-N,N-dipropyl-p-toluidine; aliphatic compounds series herbicides such as trichloroacetic acid, 2,2-dichloropropionic acid and 2,2,3,3-tetrafluoropropionic acid; 5-tert-butyl-3-(2,4-dichloro-5-isopropoxyphenyl)-1,3,4-oxadiazolin-2-one; 3-isopropyl-1H-2,1,3-benzothiadiazin (4)-3H-one-2,2-dioxide; 2,6-dichlorobenzonitrile; α-(β-naphthoxy)propionanilide; 4'-(phenylsulfonyl)-(1,1,1-trifluoromethylsulphono)-O-toluidide; 4-(2,4-dichlorobenzoyl)-1,3-dimethylpyrazole-5-yl-p-toluenesulfonate; N-p-chlorobenzyloxyphenyl-Δ'-tetrahydrophthalimide and the like. But, the herbicides are not of course limited to these examples.

The herbicides of the invention may be applied together with fungicides, pyrethroid series insecticides, other insecticides, plant growth regulators, fertilizers, etc.

When the N-dimethylbenzylacetamide derivative (I) is used as a herbicide, it may be applied before or after germination of weeds in an amount within a wide range. The amount may be usually from about 0.1 to 1 kilogram per hectare, preferably from about 0.25 to 5 kilograms per hectare.

Some test examples which show the herbicidal activity of the N-dimethylbenzylacetamide derivatives (I) are shown in the following Examples wherein % is by weight.

EXAMPLE I

A Wagner's pot of 14 cm in diameter was filled with 1.5 kg of paddy field soil and added with water to make paddy field conditions. Rice seedlings of 3-leaf growth stage were transplanted in the pot, and seeds of barnyard grass (*Echinochloa cruss-galli*) and *Scirpus Hotarui*, and buds of slender spikerush (*Eleocharis aciculalis*), which tided over the winter, were further sowed therein. A required amount of each test compound was applied to the soil under water-lodged condition. Twenty-five days after the application, the herbicidal activity and phytotoxicity of the test compound were checked on the transplanted and sowed plants and spontaneously germinated *Monochoria vaginalis*. The results are shown in Table 2.

As to the application, a wettable powder containing a required amount of the test compound was diluted with water and applied in a proportion of 10 ml/pot by means of a pipette. The herbicidal activity was evaluated in figures ranging from 0 to 5.

| Figures | Percentage of inhibition (%) |
|---|---|
| 0 | 0-9 |
| 1 | 10-29 |
| 2 | 30-49 |
| 3 | 50-69 |
| 4 | 70-89 |
| 5 | 90-100 |

As to the evaluation of phytotoxicity, the three factors (i.e. height of plant, number of tillers and total weight (dry weight)) were each checked, and a ratio of the treated plot to the untreated plot was calculated for each factor. The phytotoxicity was evaluated based on the lowest value of the three ratios which was classified into the following grades ranging from 0 to 5.

| Grade | Ratio of the untreated plot (%) |
|---|---|
| 0 | 100 |
| 1 | 90-99 |
| 2 | 80-89 |
| 3 | 60-79 |
| 4 | 40-59 |
| 5 | 0-39 |

TABLE 2

| Compound No. | Dosage (weight of active ingredient, g/are) | Herbicidal activity | | | | Phytotoxicity Rice plant |
|---|---|---|---|---|---|---|
| | | Barnyard grass | Monochoria vaginalis | Scirpus Hotarui | Slender spikerush | |
| 1 | 40 | 5 | 5 | 5 | 5 | 0 |
| | 20 | 3 | 5 | 4 | 5 | 0 |
| 2 | 40 | 5 | 4 | 5 | 5 | 0 |
| | 20 | 3 | 4 | 4 | 4 | 0 |
| 3 | 80 | — | 5 | 5 | 5 | 0 |
| | 40 | — | 4 | 5 | 5 | 0 |
| 4 | 40 | 5 | 5 | 5 | 5 | 0 |
| | 20 | 5 | 5 | 5 | 5 | 0 |
| 5 | 40 | — | 5 | 5 | 5 | 0 |
| | 20 | — | 4 | 5 | 5 | 0 |
| 6 | 40 | 5 | 5 | 5 | 5 | 0 |
| | 20 | 5 | 4 | 5 | 5 | 0 |
| 7 | 20 | 5 | 5 | 5 | 5 | 0 |
| | 10 | 4 | 4 | 5 | 5 | 0 |
| 8 | 20 | 5 | 5 | 5 | 5 | 0 |
| | 10 | 4 | 4 | 5 | 4 | 0 |
| 9 | 20 | 5 | 5 | 5 | 5 | 0 |
| | 10 | 4 | 4 | 5 | 5 | 0 |
| 10 | 40 | 5 | 4 | 5 | 5 | 0 |
| | 20 | 4 | 4 | 4 | 5 | 0 |
| 11 | 40 | — | 4 | 5 | 5 | 0 |
| | 20 | — | 4 | 5 | 4 | 0 |
| 12 | 40 | 5 | 5 | 5 | 5 | 0 |
| | 20 | 4 | 5 | 5 | 5 | 0 |
| 13 | 40 | 5 | 5 | 5 | 5 | 0 |
| | 20 | 5 | 4 | 5 | 5 | 0 |
| 14 | 20 | 4 | 4 | 5 | 5 | 0 |
| | 10 | 3 | 4 | 4 | 5 | 0 |
| 15 | 20 | 5 | 5 | 5 | 5 | 0 |
| | 10 | 5 | 4 | 5 | 5 | 0 |
| 16 | 20 | 5 | 5 | 5 | 5 | 0 |
| | 10 | 5 | 5 | 5 | 5 | 0 |
| 17 | 40 | 5 | 5 | 5 | 5 | 0 |
| | 20 | 5 | 5 | 5 | 5 | 0 |
| 18 | 20 | 5 | 5 | 5 | 5 | 0 |
| | 10 | 5 | 5 | 5 | 5 | 0 |
| 19 | 40 | 5 | 5 | 5 | 5 | 0 |
| | 20 | 5 | 4 | 5 | 5 | 0 |
| 20 | 40 | 5 | 5 | 5 | 5 | 0 |
| | 20 | 5 | 5 | 5 | 4 | 0 |
| 21 | 40 | 5 | 5 | 5 | 5 | 0 |
| | 20 | 4 | 5 | 5 | 5 | 0 |
| 22 | 40 | 5 | 5 | 5 | 5 | 0 |
| | 20 | 5 | 4 | 5 | 5 | 0 |
| 23 | 80 | — | 5 | 5 | 5 | 0 |
| | 40 | — | 4 | 5 | 5 | 0 |
| 24 | 80 | — | 5 | 5 | 5 | 0 |
| | 40 | — | 5 | 5 | 5 | 0 |
| 25 | 80 | — | 5 | 5 | 5 | 0 |
| | 40 | — | 5 | 5 | 5 | 0 |
| 26 | 80 | — | 5 | 5 | 5 | 0 |
| | 40 | — | 4 | 5 | 4 | 0 |
| 27 | 80 | — | 4 | 5 | 5 | 0 |
| | 40 | — | 4 | 4 | 5 | 0 |
| 28 | 40 | 5 | 5 | 5 | 5 | 0 |
| | 20 | 4 | 4 | 5 | 5 | 0 |
| 29 | 80 | 5 | 5 | 5 | 5 | 0 |
| | 40 | 4 | 5 | 5 | 4 | 0 |
| 30 | 40 | 5 | 5 | 5 | 5 | 0 |
| | 20 | 5 | 5 | 5 | 5 | 0 |
| 31 | 40 | 5 | 4 | 5 | 5 | 0 |
| | 20 | 5 | 4 | 5 | 5 | 0 |
| 32 | 40 | 5 | 5 | 5 | 5 | 0 |
| | 20 | 5 | 5 | 5 | 5 | 0 |
| 33 | 40 | 5 | 5 | 5 | 5 | 0 |
| | 20 | 4 | 4 | 5 | 5 | 0 |
| 34 | 20 | 5 | 5 | 5 | 5 | 0 |
| | 10 | 5 | 5 | 5 | 5 | 0 |
| 35 | 20 | 5 | 5 | 5 | 5 | 0 |
| | 10 | 5 | 5 | 5 | 4 | 0 |
| 36 | 40 | — | 5 | 5 | 5 | 0 |
| | 20 | — | 4 | 5 | 5 | 0 |
| 37 | 80 | 5 | 5 | 5 | 5 | 0 |
| | 40 | 5 | 5 | 5 | 5 | 0 |
| 38 | 20 | 5 | 5 | 5 | 5 | 0 |
| | 10 | 4 | 4 | 5 | 5 | 0 |
| 39 | 40 | 5 | 5 | 5 | 5 | 0 |
| | 20 | 4 | 5 | 5 | 5 | 0 |
| 40 | 40 | 5 | 5 | 5 | 5 | 0 |
| | 20 | 4 | 5 | 5 | 5 | 0 |
| 41 | 20 | 5 | 5 | 5 | 5 | 0 |
| | 10 | 5 | 4 | 5 | 5 | 0 |
| Untreated | — | 0 | 0 | 0 | 0 | 0 |

EXAMPLE II

The seeds of weeds such as large crabgrass (*Digitaria sanguinalis*), redroot pigweed (*Amaranthus retroflexus*), tubers of purple nutsedge (*Cyperus rotundus*) and seeds of crops such as peanut and cotton were each sowed in a 10 cm flower pot and covered with soil. Separately, a required amount of each test compound was formulated into an emulsifiable concentrate and diluted with water. The diluted chemical solution was applied to the soil by means of a hand sprayer and the thus treated soil was mixed and kept to the depth of 2 cm from the soil surface. Each of the weeds and crops was grown up in a green-house, and the herbicidal activity and phytotoxicity of the test compound were checked 20 days after the application. The test results are shown in Table 3. The herbicidal activity was evaluated in figures ranging from 0 to 5. The phytotoxicity to the crop plants was also indicated on the same standard as that of the herbicidal activity.

| Figures | Percentage of inhibition (%) |
|---|---|
| 0 | 0-9 |
| 1 | 10-29 |
| 2 | 30-49 |
| 3 | 50-69 |
| 4 | 70-89 |

-continued

| Figures | Percentage of inhibition (%) |
|---|---|
| 5 | 90–100 |

TABLE 3

| Compound No. | Dosage (weight of active ingredient, g/are) | Herbicidal activity Purple nutsedge | Large crabgrass | Redroot pigweed | Phytotoxicity Peanut | Cotton |
|---|---|---|---|---|---|---|
| 1 | 80 | 5 | 4 | 4 | 0 | 0 |
|  | 40 | 4 | 3 | 3 | 0 | 0 |
| 3 | 80 | 5 | 5 | 5 | 0 | 0 |
|  | 40 | 5 | 4 | 4 | 0 | 0 |
| 4 | 80 | 5 | 5 | 5 | 0 | 0 |
|  | 40 | 5 | 5 | 5 | 0 | 0 |
| 6 | 80 | 5 | 5 | 4 | 0 | 0 |
|  | 40 | 5 | 4 | 4 | 0 | 0 |
| 7 | 80 | 5 | 4 | 4 | 0 | 0 |
|  | 40 | 5 | 4 | 4 | 0 | 0 |
| 8 | 80 | 5 | 5 | 5 | 0 | 0 |
|  | 40 | 5 | 4 | 4 | 0 | 0 |
| 9 | 80 | 5 | 5 | 5 | 0 | 0 |
|  | 40 | 5 | 4 | 4 | 0 | 0 |
| 12 | 80 | 5 | 5 | — | 0 | 0 |
|  | 40 | 5 | 4 | — | 0 | 0 |
| 14 | 80 | 5 | 5 | 5 | 0 | 0 |
|  | 40 | 5 | 4 | 5 | 0 | 0 |
| 16 | 80 | 5 | 5 | 5 | 0 | 0 |
|  | 40 | 5 | 5 | 5 | 0 | 0 |
| 17 | 80 | 5 | 5 | 5 | 0 | 0 |
|  | 40 | 5 | 5 | 5 | 0 | 0 |
| 18 | 80 | 5 | 5 | 5 | 0 | 0 |
|  | 40 | 5 | 5 | 5 | 0 | 0 |
|  | 20 | 5 | — | — | — | — |
|  | 10 | 5 | — | — | — | — |
| 22 | 80 | 5 | 5 | 4 | 0 | 0 |
|  | 40 | 5 | 4 | 4 | 0 | 0 |
| 23 | 80 | 5 | 5 | 5 | 0 | 0 |
|  | 40 | 5 | 5 | 4 | 0 | 0 |
|  | 20 | 5 | — | — | — | — |
|  | 10 | 5 | — | — | — | — |
| 24 | 80 | 5 | 5 | 5 | 0 | 0 |
|  | 40 | 5 | 5 | 4 | 0 | 0 |
|  | 20 | 5 | — | — | — | — |
|  | 10 | 5 | — | — | — | — |
| 25 | 80 | 5 | 5 | 5 | 0 | 0 |
|  | 40 | 5 | 5 | 4 | 0 | 0 |
|  | 20 | 5 | — | — | — | — |
|  | 10 | 5 | — | — | — | — |
| 26 | 80 | 5 | 5 | 4 | 0 | 0 |
|  | 40 | 5 | 5 | 4 | 0 | 0 |
| 27 | 80 | 5 | 5 | 4 | 0 | 0 |
|  | 40 | 4 | 4 | 3 | 0 | 0 |
| 28 | 80 | 5 | 4 | 5 | 0 | 0 |
|  | 40 | 4 | 4 | 3 | 0 | 0 |
| 30 | 80 | 5 | 5 | 5 | 0 | 0 |
|  | 40 | 5 | 5 | 5 | 0 | 0 |
| 32 | 80 | 5 | 5 | 5 | 0 | 0 |
|  | 40 | 5 | 5 | 5 | 0 | 0 |
| 34 | 80 | 5 | 4 | 4 | 0 | 0 |
|  | 40 | 4 | 4 | 4 | 0 | 0 |
| 35 | 80 | 5 | 5 | 5 | 0 | 0 |
|  | 40 | 5 | 4 | 5 | 0 | 0 |
| 39 | 80 | 5 | 4 | 4 | 0 | 0 |
|  | 40 | 4 | 4 | 3 | 0 | 0 |
| 41 | 80 | 5 | 5 | 5 | 0 | 0 |
|  | 40 | 5 | 5 | 4 | 0 | 0 |
| A*(1) | 80 | 0 | 0 | 1 | 0 | 0 |
|  | 40 | 0 | 0 | 0 | 0 | 0 |
| B*(2) | 80 | 0 | 3 | 3 | 3 | 2 |
|  | 40 | 0 | 2 | 1 | 2 | 1 |
| C*(3) | 80 | 0 | 0 | 0 | 0 | 0 |
|  | 40 | 0 | 0 | 0 | 0 | 0 |
| D*(4) | 80 | 0 | 0 | 1 | 1 | 1 |
|  | 40 | 0 | 0 | 0 | 0 | 0 |
| E*(5) | 80 | 0 | 0 | 0 | 0 | 0 |
|  | 40 | 0 | 0 | 0 | 0 | 0 |

TABLE 3-continued

| Compound No. | Dosage (weight of active ingredient, g/are) | Herbicidal activity Purple nutsedge | Large crabgrass | Redroot pigweed | Phytotoxicity Peanut | Cotton |
|---|---|---|---|---|---|---|

Note:
*(1)Compound disclosed in Japanese Patent Publication (unexamined) No. 88228/1973:

t-C$_4$H$_9$CONHCH$_2$—

*(2)Compound disclosed in U.S. Pat. No. 3,498,781:

t-C$_4$H$_9$CONH—C—

*(3)Compound disclosed in J. Am. Chem. Soc., 55, 4209 (1933):

t-C$_4$H$_9$CH$_2$CONH—

*(4)Compound disclosed in Japanese Patent Publication (unexamined) No. 5005/1979:

BrCH$_2$CONHCH—

*(5)Compound disclosed in Japanese Patent Publication (unexamined) No. 5005/1979:

BrCHCONHCH$_2$—

What is claimed is:

1. A compound of the formula:

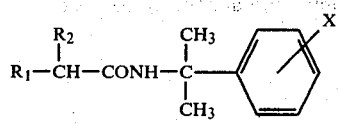

wherein X is a hydrogen atom, a methyl group, a methoxy group or a chlorine atom, R$_1$ is a C$_2$–C$_7$ alkyl group or a C$_5$–C$_7$ cycloalkyl group and R$_2$ is a hydrogen atom, a halogen atom, a C$_1$–C$_4$ alkyl group or a methoxy group, or when R$_1$ and R$_2$ are taken together, they represent a C$_4$–C$_6$ alkylene group, provided that when R$_1$ is a tertiary alkyl group, R$_2$ does not represent a halogen atom.

2. The compound according to claim 1, wherein X is a hydrogen atom or a methyl group, R$_1$ is an isopropyl group or a tert-butyl group and R$_2$ is a hydrogen atom, a methyl group, an ethyl group, an n-propyl group or an isopropyl group.

3. The compound according to claim 1, wherein X is a hydrogen atom or a methyl group, R$_1$ is an isopropyl group and R$_2$ is a bromine atom.

4. The compound according to claim 1, which is

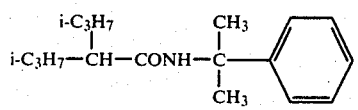

5. The compound according to claim 1, which is

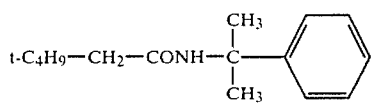

6. The compound according to claim 1, which is

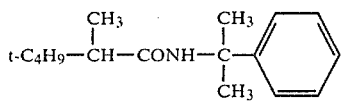

7. The compound according to claim 1, which is

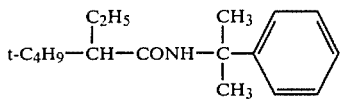

8. The compound according to claim 1, which is

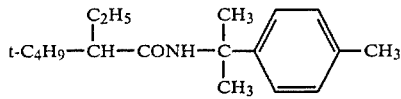

9. The compound according to claim 1, which is

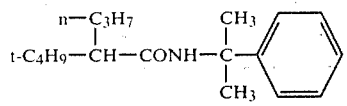

10. The compound according to claim 1, which is

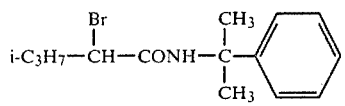

11. The compound according to claim 1, which is

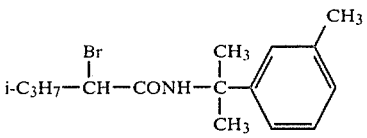

12. A herbicidal composition comprising an inert carrier or diluent and a herbicidally effective amount of at least one of the N-dimethylbenzylacetamide derivatives according to claim 1 as an active ingredient.

13. The composition according to claim 12, wherein said composition further comprises one or more additional insecticides, fungicides, nematocides, mitocides, herbicides, plant growth regulators, acaricides or fertilizers.

14. A method for controlling weeds which comprises contacting the weeds with a herbicidally effective amount of at least one of the N-dimethylbenzylacetamide derivatives according to claim 1.

* * * * *